(12) United States Patent
Potts et al.

(10) Patent No.: US 7,058,634 B2
(45) Date of Patent: Jun. 6, 2006

(54) DISTRIBUTED BLAST PROCESSING ARCHITECTURE AND ASSOCIATED SYSTEMS AND METHODS

(75) Inventors: Davin Potts, Austin, TX (US); Paul Montgomery, Austin, TX (US)

(73) Assignee: United Devices, Inc., Austin, TX (US)

( * ) Notice: Subject to any disclaimer, the term of this patent is extended or adjusted under 35 U.S.C. 154(b) by 433 days.

(21) Appl. No.: 10/360,467

(22) Filed: Feb. 6, 2003

(65) Prior Publication Data

US 2003/0149691 A1   Aug. 7, 2003

Related U.S. Application Data

(60) Provisional application No. 60/354,556, filed on Feb. 6, 2002.

(51) Int. Cl.
*G06F 7/00*    (2006.01)

(52) U.S. Cl. .......................... 707/10; 101/1; 101/104.1

(58) Field of Classification Search .................... 707/3, 707/101, 100, 1, 10, 104.1; 702/19; 435/6
See application file for complete search history.

(56) References Cited

U.S. PATENT DOCUMENTS

2001/0053957 A1* 12/2001 Blair et al. .................... 702/19

OTHER PUBLICATIONS

Darling et al., "The Design, Implementation, and Evaluation of mpiBLAST", Proceedings of Cluster World Conference & Expo, San Jose, California, Jun. 2003.*
Pedretti et al., "Three Complementary Approaches to Parallelization of Local BLAST Service on Workstation Clusters", PaCT-99, LNCS 1662, pp. 271-282, 1999.*
Zhang et al., "Transparent Checkpointing and Rollback Recovery Mechanism for Windows NT Applications", ACM SIGOPS Operating Systems Review, vol. 35, Issue 2, pp.: 78-85, Apr. 2001, ACM Press; New York, NY, USA.*
Anderson, Valerian S. & Bansal, Arvind K., "A Distributed Scheme for Efficient Pair-wise Comparison of Complete Genomes," *In the Proceedings of The International Conference of Information, Intelligence and Systems*, Washington, D.C., pp. 48-55, Nov. 1999.
BLAST "Basic Overview," Printed Jan. 29, 2002, NCBI (http://www.ncbi.nlm.nih.gov/BLAST/blast_overview.html); pp. 1-2.

(Continued)

*Primary Examiner*—Apu Mofiz
*Assistant Examiner*—Michael J. Hicks
(74) *Attorney, Agent, or Firm*—Richard F. Frankeny; Winstead Sechrest & Minick P.C.

(57) ABSTRACT

A distributed processing technique and associated method are disclosed for achieving parallel BLAST processing without requiring client systems to have direct access to the entire BLAST sequence database and without requiring significant and complex post-processing steps to obtain desired result data. More generally, a distributed processing technique and associated method are disclosed for analytical processes that require access to a massive database.

14 Claims, 5 Drawing Sheets

OTHER PUBLICATIONS

"Iterated profile searches with PSI-BLAST," Printed Feb. 1, 2002, NCBI (http://www.ncbi.nlm.nih.gov/BLAST/tutorial/Altschul-2.html); pp. 1-8.

"The Statistics of Sequence Similarity Scores," Printed Feb. 1, 2002, NCBI (http://www.ncbi.nlm.nih.gov/BLAST/tutorial/Altschul-1.html); pp. 1-13.

"The Statistics of PSI-BLAST Scores," Printed Feb. 1, 2002, NCBI (http://www.ncbi.nlm.nih.gov/BLAST/tutorial/Altschul-3.html); pp. 1-6.

"Similarity Searching: More Information," Printed Jan. 29, 2002, NCBI (http://www.ncbi.nlm.nih.gov/Education/BLASTinfor/similarity.html); pp. 1-3.

* cited by examiner

DISTRIBUTED BLAST PROCESSING ARCHITECTURE AND ASSOCIATED SYSTEMS AND METHODS

This application claims priority to the following co-pending U.S. provisional application: Provisional Application Ser. No. 60/354,556, which was filed Feb. 6, 2002, and is entitled "Distributed BLAST Processing Architecture and Associated Systems and Methods."

TECHNICAL FIELD OF THE INVENTION

This invention relates to distributed processing architectures for analytical processes that rely upon interactions with massive databases. More particularly, the present invention relates to systems, techniques and related methods for distributed BLAST processing of gene sequences.

BACKGROUND

Certain analytical processes that operate on data stored in massive databases can require queries that look to the entire database even though only segments of the entire database are being analyzed at any given moment. One significant problem associated with such analytical processes is the shear size of the massive databases. For sequential processing of such massive databases, the time to complete the analysis is often too long to be of practical use. For distributed processing of such massive databases, the time to communicate the typically required information to a plurality of processing system is often too long, making the process rather inefficient or non-feasible.

One such analytical process in the field of life sciences that utilizes a massive database is a processing algorithm known as BLAST (Basic Local Alignment Search Tool), which is available from NIH. BLAST is a heuristic search algorithm that analyzes gene sequences that are part of a massive gene library. The BLAST software code forms the analytical basis of a number of search programs, namely blastp, blastn, blastx, tblastn and tblastx. The following is a brief summary of these BLAST program variations:

blastp—compares an amino acid query sequence against a protein sequence database;
blastn—compares a nucleotide query sequence against a nucleotide sequence database;
blastx—compares the six-frame conceptual translation products of a nucleotide query sequence (both strands) against a protein sequence database;
tblastn—compares a protein query sequence against a nucleotide sequence database dynamically translated in all six reading frames (both strands); and
tblastx—compares the six-frame translations of a nucleotide query sequence against the six-frame translations of a nucleotide sequence database.

These BLAST programs ascribe significance to their findings using statistical methods and are tailored for sequence similarity searching, for example, to identify homologs to a query sequence. BLAST can use a few different input file formats, one of which is the FASTA format. The FASTA files for BLAST typically contain nucleotide, protein or amino acid data in the form of sequences. There are two sets of files which BLAST needs for a typical run: the query and the database. The query is typically a standard FASTA file, and the database is typically a set of three files which are created from a single FASTA file through the operation of the format database (formatdb) utility that is part of the BLAST software available from NIH. All four of these files are used by BLAST to produce a result file. Depending on the version of BLAST being run, there may also be a requirement for a scoring file. The BLAST result file is an application specific format that consists of header information, sequence scoring summaries, sequence details and some overall scoring data. Additional information concerning BLAST processing is available on the NIH website at the link—www.ncbi.nlm.nih.gov/blast (URL as of February 2002).

Modified BLAST processing algorithms are also available from NIH, such as a processing algorithm known as PSI-BLAST (Position Specific Iterative BLAST). PSI-BLAST refers to a feature of BLAST 2.0 in which a profile (or position specific scoring matrix, PSSM) is automatically constructed from a multiple alignment of the highest scoring hits in an initial BLAST search. The PSSM is generated by calculating position-specific scores for each position in the alignment. Highly conserved positions receive high scores and weakly conserved positions receive scores near zero. The profile is used to perform a second and further BLAST searches and the results of each "iteration" is used to refine the profile. This iterative searching strategy results in increased sensitivity.

During the BLAST or PSI-BLAST sequence analysis, the software code analyzes a query sequence against a particular segment of the gene library and makes queries that rely upon the entire gene library. Problematically, the entire BLAST sequence database will often exceed 2–3 gigabytes of data. One result of the BLAST processing which is often used by the scientists, non-profit or for-profit organizations that conduct the BLAST processing are results called the score and the "expectation value." The score represents a scoring mechanism which accounts for the length of an identified pair of similar sequences, balanced by any differences between the two sequences (as in an imperfect, but still elated matching pair). The expectation value is generally of greater interest and represents the expected number of pair-wise alignments of related sequences with a given score. The expectation value offers a measure of significance for a pair of related sequences compared to other pairs of related sequences.

Figure 1A:
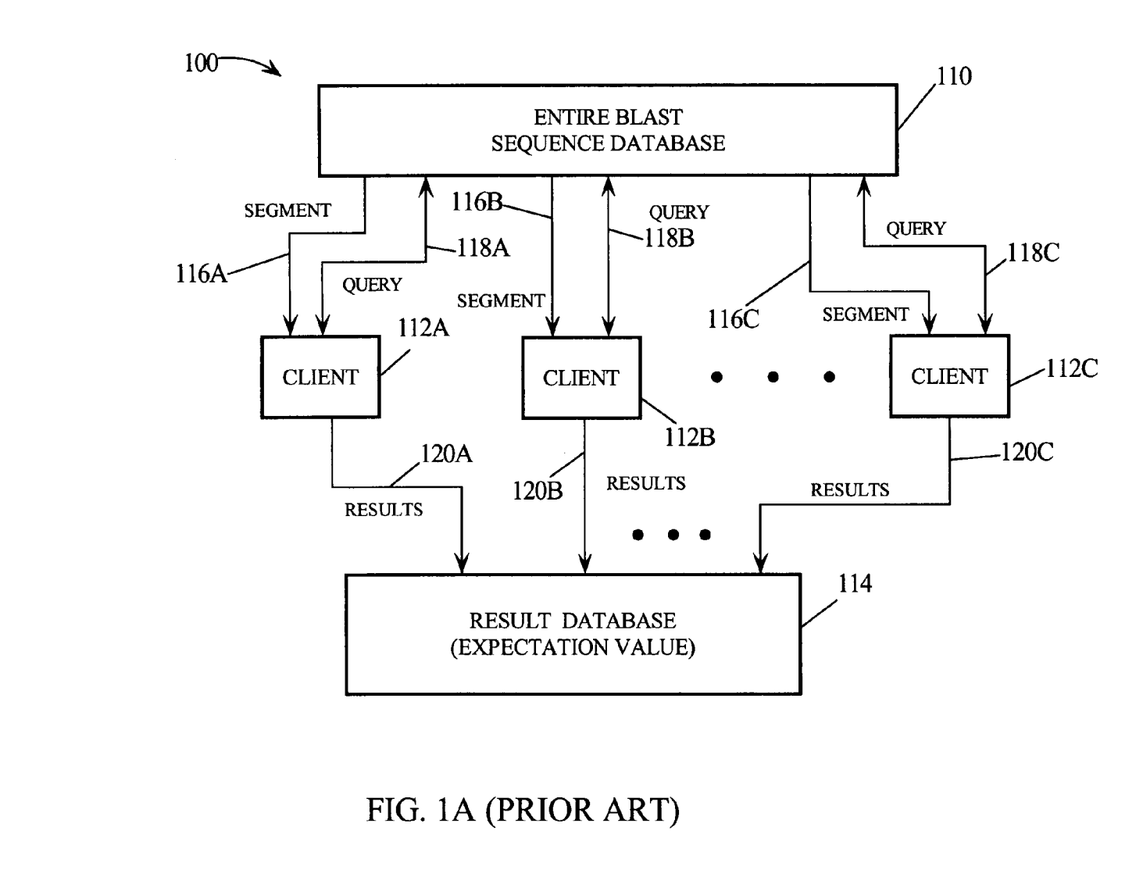
FIG. 1A (prior art) is a block diagram that represents one prior technique for decreasing the processing time by utilizing a plurality of different client machines to help process the data segments.

FIG. 1A (prior art) is a block diagram that represents one prior technique for decreasing the processing time by utilizing a plurality of different client machines to help process the data segments. Within the system 100, each client 112A, 112B . . . 112C receives a respective segment 116A, 116B . . . 116C of the sequence database 110 and processes that segment using the BLAST software code or some modification of that code. During this BLAST processing, each of the clients 112A, 112B . . . 112C makes queries 118A, 118B . . . 118C that require having access to the entire BLAST sequence database 110, which is available to each of the clients 112A, 112B . . . 112C. After processing each segment, the clients 112A, 112B . . . 112C provide results 120A, 120B . . . 120C to a result database 114. These results include the expectation values that are typically utilized, as indicated above. One significant problem with this technique is that each client must have direct access to the entire BLAST sequence database 110 during the BLAST processing. Because of the massive size of the entire BLAST sequence database, it becomes prohibitive to consider downloading a copy of the database to each client machine. Thus, this multiple-client configuration typically requires the use of a relatively small number of closely interconnected client machines that can rapidly access the entire BLAST sequence database.

Figure 1B:
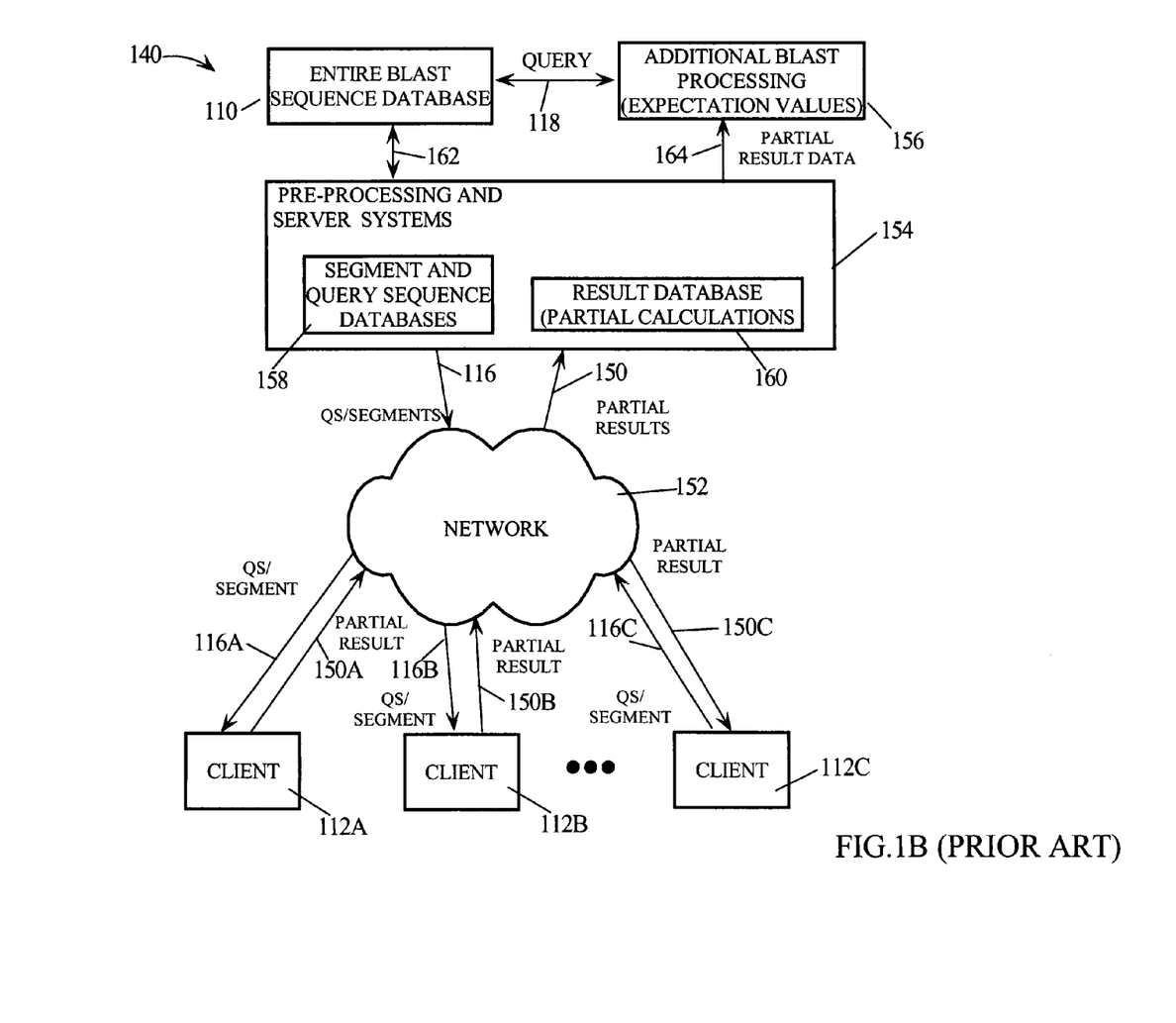
FIG. 1B (prior art) is a block diagram that represents a network-based technique for using numerous broadly distributed computers to perform partial calculations without requiring direct access to the entire BLAST database.

FIG. 1B (prior art) is a block diagram that represents a network-based technique for using numerous broadly distributed computers to perform partial calculations without requiring direct access to the entire BLAST database. Within the system 140, the pre-processing and server systems 154 has access to the entire BLAST sequence database through interface 162 and can generate segment and query sequence (QS) databases 158 that include sequence segments and query sequences that will be processed by the clients 112A, 112B . . . 112C. The server systems 154 communicates with the clients 112A, 112B . . . 112C through the network 152, which can be any of a wide variety of networks or interconnected networks structures, including the Internet. The server systems 154 transfer segments and query sequences (QS) 116 through the network so that each client receives segments and query sequences represented by lines 116A, 116B and 116C, respectively. The clients 112A, 112B . . . 112C then can conduct partial BLAST processing on these segments, but cannot complete the processing because they lack an ability to perform the necessary queries to the entire BLAST sequence database 110. Thus, only partial results 150A, 150B . . . 150C are sent back through the network and ultimately to the server systems 154, as represented by line 150. These partial BLAST calculations can then be stored in a result database 160. As represented by line 164, the partial result data can be passed along to additional BLAST processing system 156, which has direct access to the entire BLAST sequence database. By using the partial calculations and by making queries along line 118 associated with those partial calculations, the additional BLAST processing system 156 can then derive the desired results of the BLAST processing, such as producing the expectation value associated with a given gene sequence. One problem with this approach is that it requires significant additional BLAST processing to be conducted with respect to the partial result data produced by the client systems.

SUMMARY OF THE INVENTION

The present invention provides a distributed processing architecture and associated systems and methods for achieving distributed BLAST processing without requiring client systems to have direct access to the entire BLAST sequence database and without requiring significant and complex post-processing steps to obtain desired result data. More generally, the present invention provides a distributed processing technique and associated method for analytical processes that require access or queries to a massive database.

DESCRIPTION OF THE DRAWINGS

It is noted that the appended drawings illustrate only exemplary embodiments of the invention and are, therefore, not to be considered limiting of its scope, for the invention may admit to other equally effective embodiments.

DETAILED DESCRIPTION OF THE INVENTION

The present invention provides a distributed processing architecture that allows for distributed BLAST processing by client systems without requiring the client systems to have direct access to the entire BLAST sequence database. More generally, the present invention provides distributed processing techniques and associated methods for analytical processes that require access to a massive database.

It is noted that distributed computing environments can utilize a broad range of network-connected computing devices. Such a distributed processing system is described for example in co-pending application Ser. No. 09/648,832 entitled "SECURITY ARCHITECTURE FOR DISTRIBUTED PROCESSING SYSTEMS AND ASSOCIATED METHOD," which is hereby incorporated by reference in its entirety. As described more fully therein, distributed processing systems may identify the capabilities of distributed devices connected together through a wide variety of communication systems and networks and then utilize these capabilities to accomplish objectives of the distributed processing system. For example, distributed devices connected to each other through the Internet, an intranet network, a wireless network, home networks, or any other network may provide any of a number of useful capabilities to third parties once their respective capabilities are identified, organized, and managed for a desired task. These distributed devices may be connected personal computer systems (PCs), internet appliances, notebook computers, servers, storage devices, network attached storage (NAS) devices, wireless devices, hand-held devices, or any other computing device that has useful capabilities and is connected to a network in any manner. Incentives can also be provided, which may be based in part upon capabilities of the distributed devices, to encourage users and owners of the distributed devices to allow the capabilities of the distributed devices to be utilized in the distributed parallel processing system.

Figure 2A:
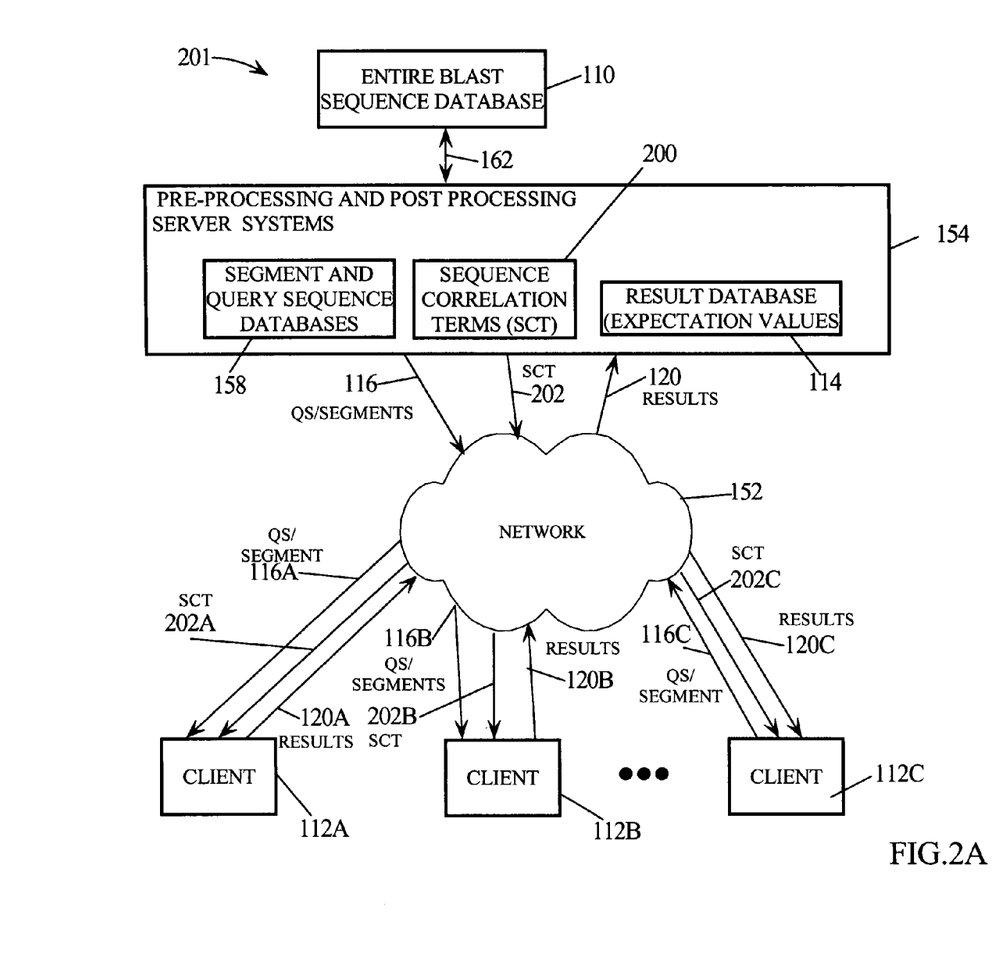
FIG. 2A is a block diagram of a parallelized BLAST processing system, according to the present invention, that allows for distributed BLAST processing without requiring direct access to the entire BLAST sequence database.

Referring now to FIG. 2A, block diagram is depicted for a parallelized BLAST processing system 201, according to the present invention, that allows for distributed BLAST processing by client systems without requiring direct access to the entire BLAST sequence database. Similar to the prior technique described in FIG. 1B (prior art), the pre-processing and server systems 154 have direct access to the entire BLAST database 110 through interface 162 and can create and can generate segment and query sequence databases 158 that include sequence segments that will be processed by the clients 112A, 112B . . . 112C. The server systems 154 communicates with the clients 112A, 112B . . . 112C through the network 152, which again can be any of a wide variety of networks or interconnected networks structures, including the Internet. The server systems 154 in FIG. 2A also transfer segments and query sequences (QS) 116 through the network so that each client receives segments and query sequences (QS) as represented by lines 116A, 116B and 116C, respectively.

Significantly different from prior techniques, however, the pre-processing and server systems 154 also determines one or more sequence correlation terms (SCTs) 200 that are provided to the network, as represented by line 202, and ultimately to the clients the clients 112A, 112B . . . 112C, as represented by lines 202A, 202B . . . 202C. These SCTs 200 represent properties of the massive BLAST sequence database 110 that are relied upon during the BLAST processing. As discussed above, the typical BLAST processing requires a query to the entire BLAST sequence database 110 in order for the processing to produce the desired analytical results, such as the expectation value for the segment being analyzed. According to the present invention, the SCTs 200 provide a proxy for this required query and access to the entire BLAST sequence database 110, thereby allowing the analytical process being conducted by BLAST to achieve the same result without requiring the query and direct access to the entire BLAST sequence database 110. Thus, the SCTs 200 provide a simplified term or property of the entire database that can be reasonably communicated across the network 152 to the clients 112A, 112B . . . 112C so that the clients 112A, 112B . . . 112C can send back the desired results 120A, 120B . . . 120C. The communication of the STCs 200 from the server systems 154 to the network 152 is represented by the line 202. And the communication to the clients 112A, 112B . . . 112C is represented by the lines 202A, 202B . . . 202C, respectively.

The results database 114, therefore, includes the desired results, such as expectation values, without requiring significant additional BLAST processing and BLAST processing queries to entire BLAST sequence database 110. Thus, although additional post-processing may be done on the result data if desired, it is not required in order to achieve desired and useful results directly from the processing performed by the client systems 112A, 112B . . . 112C. It is further noted that, if desired, the SCTs 200 can also be configured to provide a proxy or simplification of the required query such that the results achieved are as similar as desired, although not identical, to the typical BLAST results. In other words, if identical results are not necessary, the SCTs 200 can be configured to provide an approximation of the results that would be achieved in the standard processing.

Figure 2B:
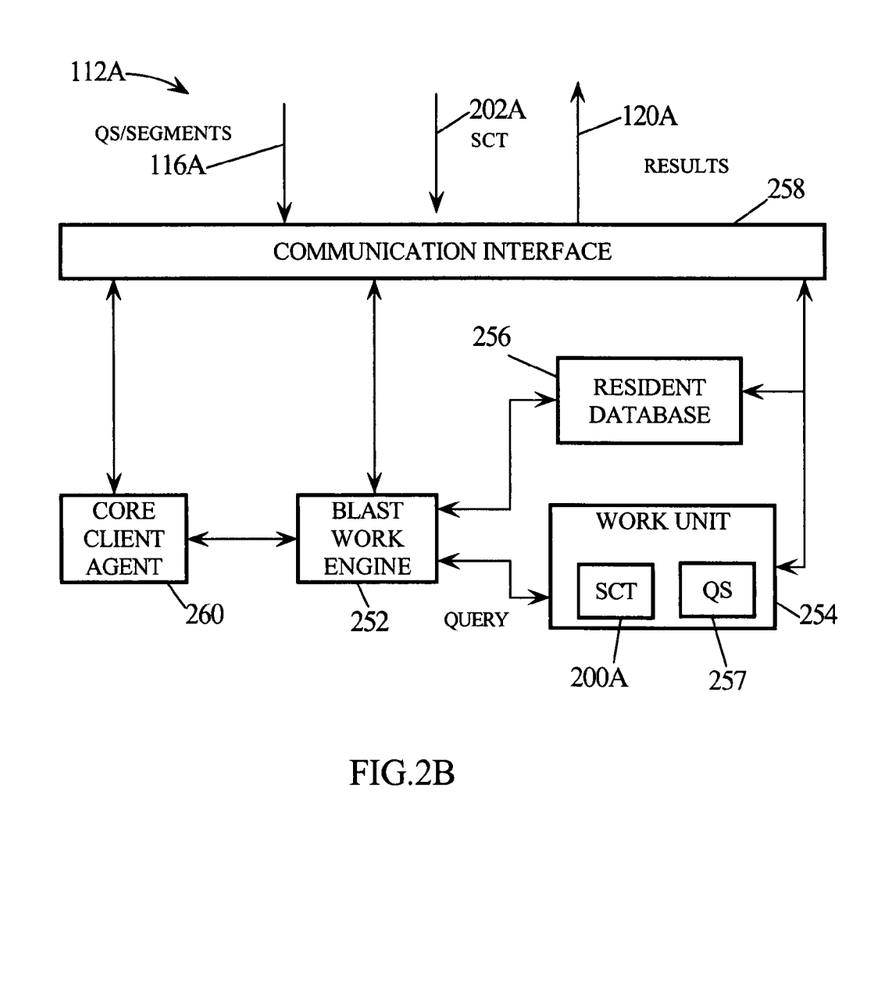
FIG. 2B is a block diagram of a client system that utilizes a sequence correlation term (SCT) so that direct access to the entire BLAST sequence database is not required in order to produce desired result data, such as expectation values.

FIG. 2B is a block diagram of a client system that utilizes a sequence correlation term (SCT) so that direct access to the entire BLAST sequence database is not required in order to produce desired result data, such as expectation values. The example client system 112A includes a communication interface 258 through which the client system 112A communicates to the network 152. These communications, for example, can include receiving segments and query sequences and the SCTs as represented by lines 116A and 202A, respectively, and sending back results, as represented by line 120A. In addition, the client system 112A can include a core client agent component 260 and BLAST work engine component 252 that conducts the BLAST analytical processing. Data for the BLAST processing can be stored in a resident database (resdata) 256. This data can include segments of the sequence database and/or other data that is used in the BLAST processing. In addition, the query sequence 257 and the SCT 200A can also be stored locally as part of the workunit 254. If desired, the resdata 256 can also be considered part of the workunit 254, and the workunit 254 can also include other information that is used to conduct the BLAST processing. In transferring information through the network to the client 112A, the resdata 256, the work engine 252 and the SCT 200A can be combined for transfer as a single workunit file. Advantageously, having the SCT data 200A stored or accessible locally allows for the BLAST processor kernel 252 to conduct the BLAST processing on the segment of the sequence database by making an appropriate query utilizing the SCT data 200A from block 254 without requiring access back to the entire BLAST sequence database 110.

It is further noted that BLAST conventionally attempts to use several resource files to load information about its environment and where relevant files are located. BLAST also conventionally utilizes an input file for this processing. Thus, as stated above, these conventional resource files and input data files (e.g., the QS 257) can be included with one non-conventional control file (e.g., the SCT 200A) to constitute a single workunit 254 for each client 112A, 112B . . . 112C. The non-conventional control file, such as the sequence correlation term (SCT) 200A, contains statistically relevant information about the complete sequence database that the input sequences are searching against. As such, this non-conventional control file and associated SCTs can be updated at planned times and/or when the entire BLAST sequence database 110 grows. This updating can be the duty of the BLAST-specific preprocessing application that is part of block 154 in FIG. 2A. With respect to the conventional resource files, they can be configured to reflect a mundane environment where all relevant files are located in the current working directory and are named according to some fixed pattern. If desired, compression algorithms, such as BZIP2 can be utilized to send data to the client machines; however, it is noted that the input data files may often be too small to warrant effective use of BZIP2 compression.

An example sequence correlation terms 200 that may be utilized for BLAST processing is now discussed in more detail. The expectation value for a pair of aligned sequences identified by the BLAST processing may be expressed as a product of three separate mathematical terms: a constant, a correlation term, and a term which depends upon the score. Of these three terms, only the correlation term has any dependency on sequences stored in the database beyond the pair of aligned sequences of immediate interest. This sequence correlation term offers a means of correlating the significance of a pair of aligned sequences of interest against all other possible alignments of varying scores possible from the entire database of sequences. To compute this correlation term, the conventional approaches taken in the various BLAST programs make use of statistical properties of the entire database, the length of the database taken as if it were a single long sequence and the number of individual sequences in the database. Otherwise, as recognized in the present invention, the calculation of the correlation term does not depend upon other information from the database and does not depend upon specific pairs of aligned sequences found during runs of BLAST. It should be noted that the correlation term does additionally depend upon the particular BLAST method invoked in the BLAST program (e.g., blastp, blastn, blastx, tblastn, tblastx). The remaining two terms, the constant and the term dependent upon the score, are calculated independent of the entire database using only the input data available from 112A, 112B . . . 112C.

Thus, as recognized and implemented in the present invention, direct access to the entire database is not necessary for BLAST if the correlation term is provided through operation of the sequence correlation term (SCT) block 200.

Calculation of the sequence correlation term in SCT block 200 as part of the pre-processing system 154 requires a relatively small effort, and the SCT can then be provided to the clients 112A, 112B ... 112C for local use as indicated by lines 201A, 201B ... 201C. It is further recognized that the clients 112A, 112B ... 112C can also calculate the SCT locally for use in the BLAST processing. In this alternative processing scheme, the relevant statistical properties of the entire database may be provided from the pre-processing system 154 to the clients 112A, 112B ... 112C as part of the control files and/or as part of the workunit packages that are provided to clients 112A, 112B ... 112C. The clients 112A, 112B ... 112C can then locally use this statistical database property information to generate the SCT that the clients 112A, 112B ... 112C then use in their local BLAST processing. This alternative processing technique would, therefore, move part or all of the SCT determination from the pre-processing system 154 to the clients 112A, 112B ... 112C. It is further noted that other techniques for generating the SCT and providing the SCT to the clients 112A, 112B ... 112C could also be utilized, if desired, with the result being that the clients 112A, 112B ... 112C can utilize the SCT or other database property in its processing without requiring access to the massive database itself.

Looking now more particularly to the resident database (resdata) 256, it is noted that this resdata 256 can be configured to consist of a single file containing a section of the complete BLAST sequence database 110. This section or segment of data can be retained in its standard FASTA format so that no additional information is required by the BLAST processing engine 252 to determine which fragment of the complete database it might be. The relevant information regarding the size of the overall database is instead communicated as part of the workunit 254, for example, in the form of the SCT.

In operation, the communication of data from the server systems 154 to the client machines 112A, 112B ... 112C can be accomplished in a fashion as to improve the reliability of those communications. Although the pre-processing within block 154 acts to break the complete BLAST database 110 (expected to be at least 2–6 Gb in size) into smaller fragments to be sent out as sequence segments files of some desired size, these files themselves may still exceed 30 Mb in size at a minimum to make the process efficient. As a general rule, it is expected that the larger the size of the sequence segment file or resdata, the more ultimately favorable the computation/communication ratio will be for the distributed BLAST processing system. Thus, for example, for deployment on Internet connected client machines, these resdata files will likely be large for efficiency reasons and may need to be transferred a-little-at-a-time through the use of partial file transfers. In addition, it is possible that the most desirable arrangement for partial file transfers may involve the scheduled stop and restarting of the file transfer process so that no more than a certain amount of data is transferred during a particular session, for example, for a client machine connected over a slow modem connection.

Once a machine has received one resdata file, it typically will not be sent a new BLAST-associated resdata file unless (1) all workunits have been completed against the first resdata file, or possibly (2) a third-party user's defined quota for the disk workspace allowed to be used by the distributed processing system can accommodate a second resdata file. This second case, however, introduces complications for scheduling efficiency that can be addressed through the scheduling routines used by the server systems 154. The server systems 154 can be configured to have the ability to understand that a wide variety of permutations of workunits and resdata files can be distributed for execution since any workunit associated with the $n^{th}$ resdata file can also be associated with the $(n+1)^{st}$ resdata file. This understanding can be implemented through appropriate scheduling of the workunit and resdata file transfers to the client machines 112A, 112B ... 112C. As stated above, compression algorithms can be used to reduce the size of files during transfer and for storing files, and some compression algorithms may provide better size reduction performance than others. For example, if the resdata file is stored using a BZIP2-compressed-format, this format can afford an extra 20–33% compression above that possible with GZIP at its most aggressive compression settings, given the nature of the data in the resdata file. To help gain this significant space advantage, the BLAST work engine 252 can be configured to open the BZIP2-compressed resdata file as read-only to produce a stream from the file containing its decompressed contents.

It is again noted that the complete BLAST sequence database 110 is not expected to remain static. Rather, it is expected to grow, in some environments potentially on a daily basis. However, the contents of the BLAST sequence database 110 will typically not be modified, but only concatenated with additional sequence data. Thus, the pre-processor within block 154 can be configured to add to the number of resdata files, as necessary, when the BLAST sequence database 110 increases. For example, it is expected that the entire BLAST sequence database 110 will be broken into a number of different segments in order to form the individual resdata files, which each contain a segment of the sequence. To create these resdata files, a standard file size may be selected. Thus, each resdata file can be filled with an equivalent amount of data with respect to size. Any partial sequence data left over in this process can be placed in a "final" resdata file, which will not yet be at its capacity according to the selected file size. This final resdata file can be set to expire each time an update, such as a scheduled update, from the complete BLAST sequence database 110 is made by the pre-processing engine. At each update, therefore, the final resdata file can be replaced with a new final resdata file until capacity is reached and the cycle repeats. The pre-processing scripts and submission scripts for the pre-processing and server systems 154 are configured to manage these operations. In addition, as the entire BLAST sequence database 110 changes, the pre-processing and server systems 154 will also modify the control files contained in the workunit, such as the SCTs, for all client machines that have not yet begun execution with any particular resdata file.

Another issue that can be addressed by the pre-processing and server systems 154 is the lossy compression scheme used by the typical BLAST processing scheme. In particular, BLAST typically performs a lossy compression of sequence data in its databases (much like the JPEG format vs. bitmap format in image files). When BLAST runs "formatdb" on a FASTA database sequence file containing the basepairs A, T, C, G and N, it only reproduces the A, T, C and G letters and leaves the N (standing for a wildcard) out. It substitutes either A, T, C or G in for the N so that it can keep its 4 to 1 compression (i.e., 2 bits for each letter). It chooses which letter to substitute for N randomly. BLAST does not seed the pseudo-random number generator (PRNG) which translates into always seeding to the same number by default (srandom (1)). Thus, for example, on Linux the numbers generated are deterministic (i.e., they are the same every time you run the program). This translates into the fact that no matter how many times you run "formatdb" on a sequence file, it will always produce the same results.

With respect to the distributed BLAST processing of the present invention, however, once the database file is split into smaller segments, differences in the data will be produced due to the random N replacement feature of "formatdb." For example, assume due to the deterministic nature of the PRNG function, an N replacement sequence of ATCG (repeating) will always be produced. Now assume a nonsense sequence of 10 Ns to show this example clearly— NNNNNNNNNN. No matter how many times you run "formatdb" on this sequence, the result will be ATCGATCGAT, based upon the assumption above. Next, assume that the original data is split into 2 parts—NNNNN and NNNNN. When "formatdb" is then run separately on the two parts, the result is now ATCGA for each grouping of five Ns. Thus, the first five letters for the second data segment rather than the TCGAT that occurs if all ten Ns are replaced in one execution of the "formatdb" operation. This result is caused by the PRNG function being starting from the beginning on each data segment rather than continuing as one sequence. Considering the replacement strings side by side, it is evident that differences are created between the distributed operation of BLAST and a non-distributed operation of BLST due to the split of the database into data segments.

ATCGATCGAT (example operation without data split)
ATCGAATCGA (distributed operation with data split)

The result, therefore, is that the distributed BLAST processing now has different data to work with and may produce different results than the non-distributed BLAST processing. Although both results are likely to be equally viable from a scientific standpoint, it may be desirable to have the distributed BLAST processing produce results that match the typical BLAST processing in consideration of this wildcard replacement scheme.

One example solution to this replacement discrepancy is to keep track of the number of wildcard basepair indicators within each data segment, to provide this information to the client devices, and to modify the "formatdb" program to use this information. In other words, when the pre-processing and server systems 154 break the entire BLAST sequence database 110 into data segments 116A, 116B . . . 116C, the pre-processing and server systems 154 also determine for each segment the number of wildcards that fall within that segment. For example, assume that data segment 116A has 1 N, segment 116B has 2 Ns, and segment 116C has 3 Ns. When the pre-processing and server systems 154 transmit these data segments to the clients 112A, 112B . . . 112C, the number of preceding wildcards can also be provided. Thus, client 112A would know that it had the first data segment and that no Ns preceded the Ns in data segment 116A. Client 112B would know that 1 N preceded the Ns in data segment 116B, which it received. And client 112C would know that 3 Ns preceded the Ns in data segment 116C, which it received. The modified "formatdb" program can then use this information to select the replacement basepairs that would match the replacement basepairs that would have been used in a non-distributed BLAST processing environment. In the example above, therefore, client 112A would start its replacement at the beginning of the string thereby using an A basepair to replace the N within data segment 116A. Client 112B would start its replacement with the second place in the string thereby using the TC basepairs to replace the two Ns within data segment 116B. And client 112C would start its replacement with the fourth place in the string thereby using the GA basepairs to replace the two Ns within data segment 116C. It is also noted that rather than sending the number of preceding wildcards to the clients and having the generation of the replacement string done by the clients, the appropriate replacement string could be provided to the clients by the pre-processing and server systems 154. Other variations or schemes could also be employed to facilitate the replication of the replacement strings, as desired.

Looking again at FIG. 2B, a resdata file is sent to and stored by the client 112A in the resident database 256. The workunit including the SCT 200A is similarly sent to and stored by the client in block 254. The BLAST work engine 252 uses this data to perform its BLAST processing. As part of its input, BLAST typically will read in, as parameters, certain information about the complete sequence database (for example, the size of the complete database) which otherwise would have been empirically determined at runtime from the entire BLAST sequence database 110. As discussed above, the current invention avoids this requirement of having to access the entire BLAST sequence database 110 through the use of database properties, such as the sequence correlation terms (SCTs). Because the BLAST work engine 252 will likely need to make a function call related to these term on a fairly regular basis, the function call can be defined as part of the API for the core client agent 260. In addition, circular buffers can be used to improve the performance of the processing. The output or results 120A from the client machine 112A after the BLAST processing advantageously can take the form of a single output file that contains the standard BLAST output.

During operation of the BLAST processing on the client 112A, checkpointing may be utilized to allow recovery should the process be halted due to an error before the processing of the data segment is complete. Checkpointing in the distributed BLAST can be used to occasionally save the state of the processing in order to restart the processing without losing much work in the event of a problem. Problems might range from something simple as a person rebooting their machine during a run to the problem of the machine running out of resources (such as memory) and the program crashes. To handle such problems, run progress information can be stored in a checkpoint file, and this file can be used to restart the processing near where processing was stopped, thereby saving the reprocessing time that would have normally occurred.

The checkpoint file may, for example, reside on the client machine in an encrypted format. This file may store a sequence number and a file position as the checkpoint, and this information can be used to restart BLAST processing where an error or other event caused the processing to stop. The sequence number represents the number of the sequences (starting at 1) from the query (workunit) that was last completed successfully. In BLAST, each sequence in the query (workunit) is compared against all of the sequences from the database (resdata) before proceeding to the next sequence in the query. This point can be saved and used, for example, to provide the information concerning the state of processing. This information can then be used to skip ahead in the processing to the next unprocessed record. The file position represents the position in the results file at the end of the last successfully written result. This allows the BLAST processing to be restarted and result data to be written to the result file in the correct position even if the BLAST processing were in the middle of writing out data when the previous run was halted. In addition, as an extra precaution in the case of an invalid or partial checkpoint file, XML-like tags can be used around the data. If the tag does not exist, the entire checkpoint file can be thrown away, and the processing can be started at the beginning. This further precaution can be used to provide an increased level of assurance of data integrity.

Looking back to FIG. 2B, after receiving the BLAST result files 120 from the clients 112A, 112B . . . 112C and storing them in the results database 114, a post-processing program can be utilized to format or further process the data. For example, the post-processing can appropriately combine the returned outputs with other outputs to achieve a standard sequential BLAST results file. The timing of this post-processing can be configured, for example, to be triggered by the results database 114 receiving final relevant results or to check at a scheduled intervals to see if all of the results for a particular workunit have been received. The post-processing can combine results from a multiple-resdata-singlework-unit combination to produce a single output file that would match a single-resdata-single-workunit output that would be expected from sequential BLAST processing. Thus, advantageously, a single output file can be configured by post-processing within the server systems 154 to contain the standard BLAST output. In addition, if an error is determined in the result data, the post-processing within block 154 can be configured to indicate to the database, or to modify the database directly, such that a particular workunit will be rescheduled for additional runs against certain resdata files. Other post-processing activities can be configured, as desired, within the pre-processing and post-processing server systems 154.

Figure 3:
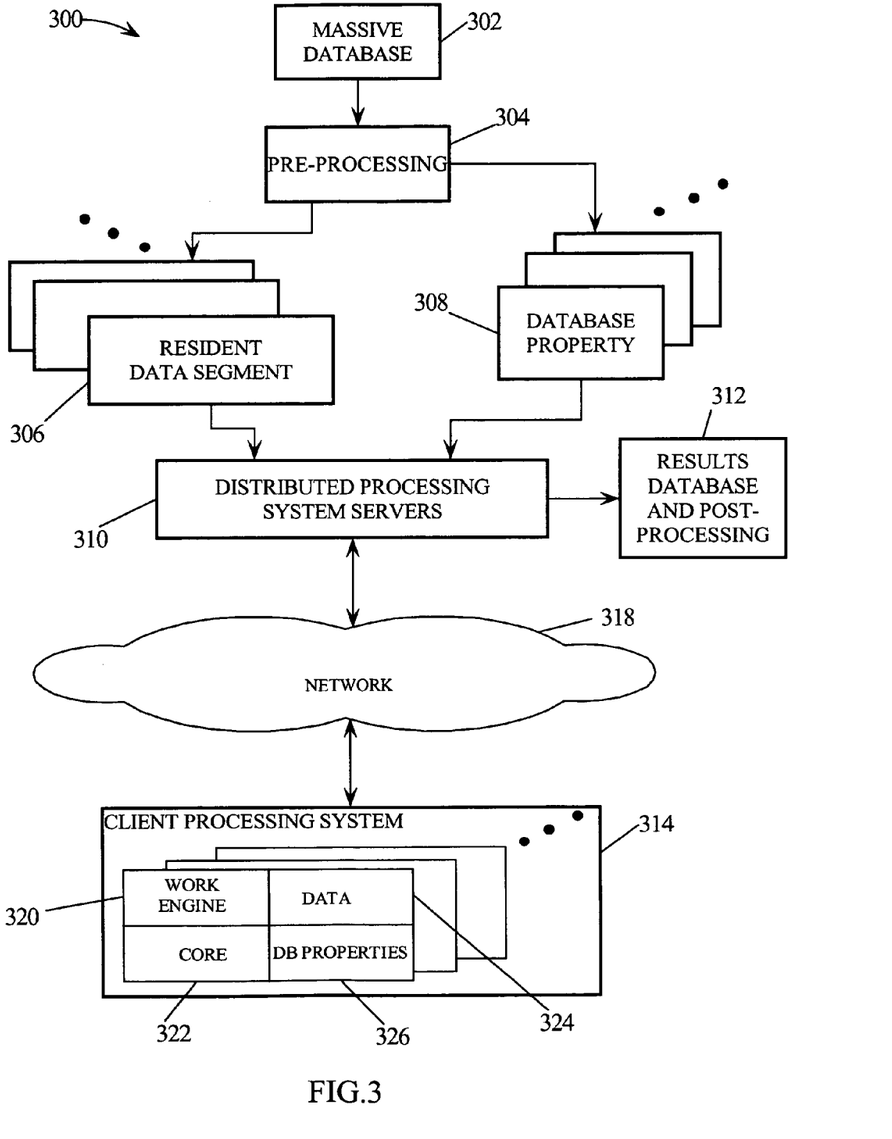
FIG. 3 is a block diagram of a more general distributed processing system, according to the present invention, that allows parallelized processing for analytical processes that typically require access to a massive database.

FIG. 3 is a block diagram of a more general distributed processing system 300, according to the present invention, that allows distributed processing by remote client systems for analytical processes that typically require access and queries to a massive database. The massive database 302 is first processed by pre-processing block 304 to prepare the data that will be needed for the distributed processing. One key feature to this system is the ability to determine from the analytical process what aspects of the massive database 302 are used in the analytical process. Thus, in addition to breaking the massive database 302 into number of different resident data segments 306, the pre-processing block 304 also analyzes the massive database 302 to determine one or more database properties 308 that will be utilized by the analytical process when it is performed remotely on the many different client machines 316. Distributed processing system servers 310 act to distribute, schedule and otherwise facilitate the flow of information to and from the client processing systems 314 through the network 318. The information provided to each client system 316 can include data 306 and at least one database property 326.

The client processing systems 314 include a number of different clients 316. As shown in FIG. 3, each client 316 can include a number of different functional blocks, for example, a core client agent 322, a work engine 320, data 324 and database property 326. When the work engine 320 executes to operate the analytical process on the stored data within block 324, the work engine 320 uses the database properties 326 rather than requiring an access back to the massive database 302. Thus, by identifying the properties of the massive database 302 actually needed by the analytical process run by the work engine 320 and by sending those properties to the remote clients 316 along with the data 324 to be processed, the present invention significantly improves the communication-to-processing-time efficiency of the distributed computing process. It is noted that in correlation to FIG. 2B, the database property 326 can be viewed as including the SCT 200A, and the data 324 can be viewed as including any other data transferred, such as the resdata 256, the query sequence 257, other files within workunit 254 and any other data desired to be part of the resident database 256 and/or the workunit 254.

The results received back through the network 318 from the client processing systems 314 may be stored in a results database represented by block 312. Depending upon the database properties identified and used as a proxy for the conventional access and query utilized by the analytical process, the results may be identical to, or merely an approximation of, the results that would have been achieved in a non-distributed-processing architecture. These results may also be subjected to additional post-processing, if desired, as represented by block 312. This post-processing, for example, could be to combine the different results received from the numerous different client systems 316 into a single output file for later use.

It is noted that some analytical processes that rely upon massive databases may not lend themselves to the present invention. This may be so where there exists no discernable method for simplifying the required access to the massive database 302 into one or more database properties 308 that can be efficiently communicated to the client processing systems 314. Many analytical processes, such as the BLAST processing discussed above, however, do lend themselves to such techniques so that the same results, or results that are a close-enough approximation, can be achieved by using database properties rather than requiring direct access to the massive database 302 during run-time for the client system work engine.

Further modifications and alternative embodiments of this invention will be apparent to those skilled in the art in view of this description. It will be recognized, therefore, that the present invention is not limited by these example arrangements. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the implementations and architectures for database processing. For example, equivalent elements may be substituted for those illustrated and described herein, and certain features of the invention may be utilized independently of the use of other features, all as would be apparent to one skilled in the art after having the benefit of this description of the invention.

What is claimed is:

1. A distributed BLAST processing system, comprising:
a pre-processing system coupled to a BLAST sequence database and configured to generate a plurality of data segments, each segment including a portion of the BLAST sequence database, and configured to determine a sequence correlation term based upon properties of the BLAST sequence database; and
a server system configured to communicate with a plurality of distributed client systems, the server system further being configured to send data segments, query sequences, and the sequence correlation term to the distributed client systems and to receive BLAST result data from the distributed client systems without requiring the distributed client systems to access the BLAST sequence database; and
a plurality of distributed client systems configured to communicate with the server system through a network, each client system further being configured to receive at least one data segment and the sequence correlation term from the server system and being configured to conduct BLAST processing on the data segment utilizing the sequence correlation term without requiring access to the BLAST sequence database, wherein the server system is further configured to send a client agent component and a BLAST work engine component to the plurality of distributed client systems, and wherein the pre-processing system is further configured to determine a number of preceding wildcard basepairs associated with each data segment, wherein the server system is further configured to send a preceding wildcard number along with each data segment, and wherein the BLAST work engine comprises a wildcard basepair replacement routine that utilizes the preceding wildcard number to choose where to start in a predetermined string of replacement basepairs.

2. The distributed BLAST processing system of claim 1, wherein the BLAST result data comprises expectation values.

3. The distributed BLAST processing system of claim 2, further comprising a post-processing system configured to receive and compile the BLAST result data.

4. The distributed BLAST processing system of claim 1, wherein the network comprises the Internet.

5. The distributed BLAST processing system of claim 1, wherein the BLAST work engine comprises a checkpointing routine that causes progress information to be stored during BLAST processing.

6. The distributed BLAST processing system of claim 1, wherein the plurality of data segments are stored as data files having an identical size, except for a final file that is partially filled with sequence data, the final file being updated with new sequence data as such data is added to the BLAST sequence database.

7. The distributed BLAST processing system of claim 1, wherein the pre-processing system is further configured to recalculate the sequence correlation term when updates to the BLAST sequence database occur, and wherein the server system is further configured to send the updated sequence correlation term to the distributed client systems.

8. A method for distributed BLAST processing, comprising:
generating a plurality of data segments from a BLAST sequence database, each segment including, a portion of the BLAST sequence database;
calculating a sequence correlation term based upon properties of the BLAST sequence database;
communicating with a plurality of distributed client systems to send data segments, query sequences and the sequence correlation term to the distributed client systems;
receiving BLAST result data from the distributed client systems without requiring the distributed client systems to access the BLAST sequence database;
receiving, with each of a plurality of distributed client systems, at least one data segment and the sequence correlation, conducting BLAST processing on the data segment utilizing the sequence correlation term without accessing the BLAST sequence database, and sending BLAST result data back to a server system;
sending a client agent component and a BLAST work engine component to each of the plurality of distributed client systems for operation on the distributed client systems; and
determining a number of preceding wildcard basepairs associated with each data segment, sending a preceding wildcard number along with each data segment, and utilizing a wildcard basepair replacement routine within the BLAST work engine to choose where to start in a predetermined string of replacement basepairs.

9. The method of claim 8, wherein the BLAST result data comprises expectation values.

10. The method of claim 8, further comprising utilizing a checkpointing routine within the BLAST work engine to store progress information during BLAST processing.

11. A method for distributed BLAST processing, comprising:
generating a plurality of data segments from a BLAST sequence database, each segment including a portion of the BLAST sequence database;
determining properties of the BLAST sequence database needed for calculating a sequence correlation term for the BLAST sequence database;
communicating with a plurality of distributed client systems to send data segments and the calculation properties to the distributed client systems;
receiving BLAST result data from the distributed client systems without requiring the distributed client systems to access the BLAST sequence database; and
determining a number of preceding wildcard basepairs associated with each data segment, sending a preceding wildcard number along with each data segment, and utilizing a wildcard basepair replacement routine within the BLAST work engine to choose where to start in a predetermined string of replacement basepairs.

12. The method of claim 11, wherein the BLAST result data comprises expectation values.

13. The method of claim 11, further comprising, with each of a plurality of distributed client systems, receiving at least one data segment and the calculation properties, calculating the sequence correlation term, conducting BLAST processing on the data segment utilizing the sequence correlation term without accessing the BLAST sequence database, and sending BLAST result data back to a server system.

14. The method of claim 13, further comprising sending a client agent component and a BLAST work engine component to each of the plurality of distributed client systems for operation on the distributed client systems.

* * * * *